Jan. 24, 1967 D. L. ARMSTRONG Plant Pat. 2,704
ROSE PLANT
Filed Nov. 2, 1965
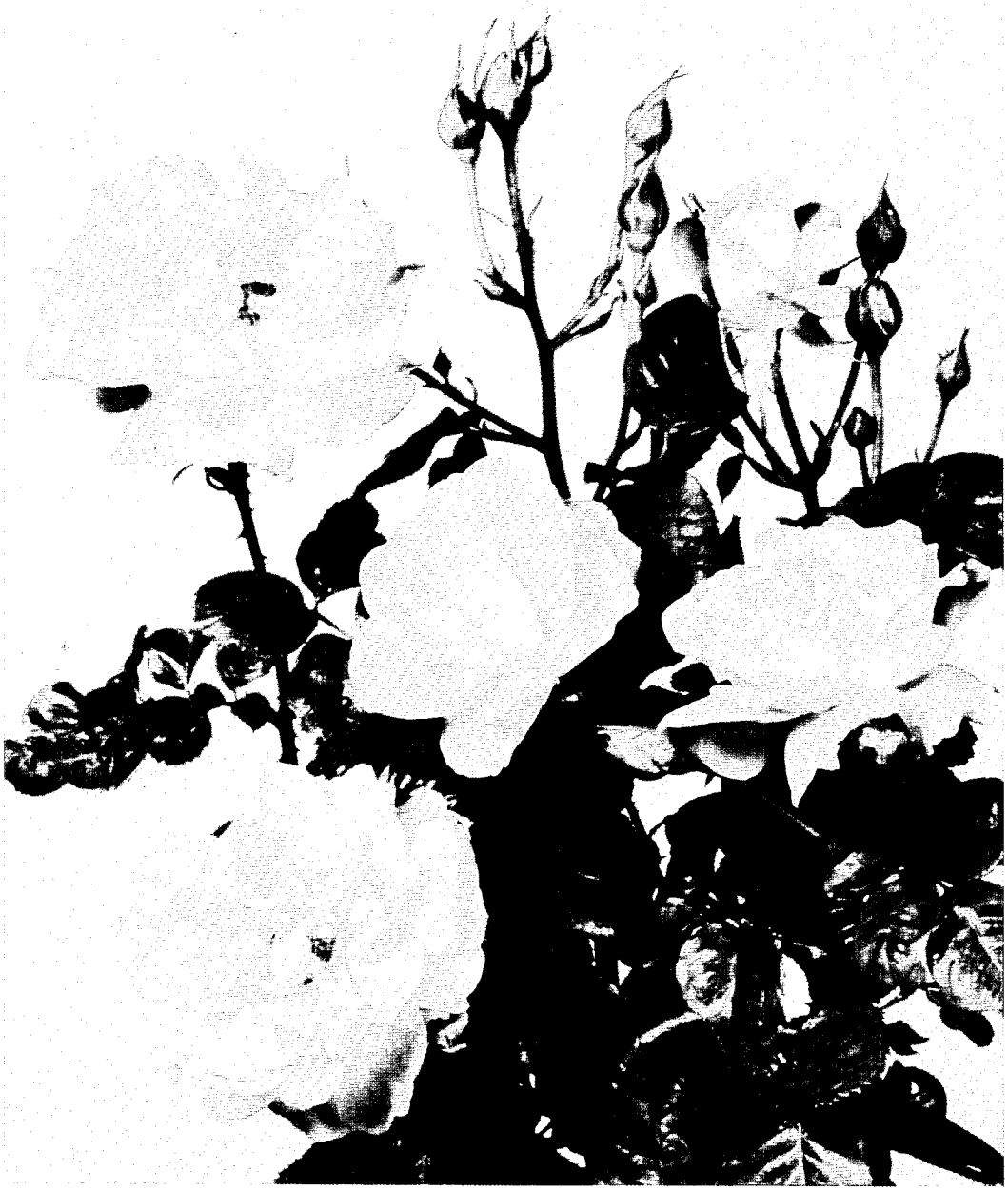
Inventor
D. L. Armstrong
By: Robb & Robb
Attorneys.

United States Patent Office

Plant Pat. 2,704
Patented Jan. 24, 1967

2,704
ROSE PLANT

David L. Armstrong, Ontario, Calif., assignor to Armstrong Nurseries, Inc., Ontario, Calif., a corporation of California Filed Nov. 2, 1965, Ser. No. 506,293
1 Claim. (Cl. Plt.—22)

The present invention relates to a new and distinct variety of rose plant of the floribunda class, which was originated by me by crossing an unnamed and unpatented rose variety of unidentified parentage with the variety known as "Circus" (Plant Patent No. 1,382), the unnamed variety being the seed parent and the variety "Circus" being the pollen parent.

The general objective of this breeding was to produce a new and improved rose variety which bears multi-colored flowers, particularly combining brilliant red colors, with the flowers being of a large size comparable to those of the seed parent, combined with the nearly perfect bud and flower form that are characteristic of the pollen parent, and still further combined with the good foliage and plant habit of both parents. This objective was fully achieved along with other desirable improvements, as evidenced by the following unique combination of characteristics which are outstanding in the new variety and which distinguish it from its parents, as well as from all other varieties of which I am aware:

(1) A very attractive, vigorous, bushy and rounded plant habit;

(2) Attractive, dense, glossy, dark green foliage which clothes the plant well;

(3) Nearly urn-shaped flower buds;

(4) Double flowers of attractive form, said flowers being of exceptionally large size for a floribunda variety, and being borne in small to medium sized clusters which cover the plant very well; and (5) A distinctive and attractive multicolored floral effect of the flowers, with red and yellow colors in the bud, red in the newly open flower, but changing to attractive pinks as the flowers age.

In comparison with its unnamed seed parent, which was a hybrid tea rose having very attractive and glossy foliage of large size and which bears large double flowers of good form with a particularly brilliant and non-bluing, medium red flower color, the new variety bears its flowers usually in clusters of from small to medium size, instead of usually singly like this parent, and the flowers of the new variety are multicolored, combining reds, yellows and pinks instead of having red flowers like those of this parent.

As compared with its pollen parent "Circus," the new variety bears larger flowers and the flowers have considerably more and darker red color than the flowers of this parent.

Asexual reproduction of my new variety by budding, as performed at Ontario, California, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Bush; outdoor; seedling; for cut flowers and for garden decoration.

Class: Floribunda.

Breeding: Seedling.

*Seed parent.*—An unnamed rose variety of unidentified parentage.

*Pollen parent.*—"Circus."

Propagation: Holds its distinguishing characteristics through succeeding propagations by budding.

*Flower*

Locality where grown and observed: Ontario, California.

Flowers borne: Sometimes singly and usually from 3 to 5 or more to stem; in irregular clusters; on strong stems of short to medium length.

Quantity of bloom: Very abundant, outdoors.

Continuity: Near continuous during growing season.

Fragrance: Slight.

Bud:

*Peduncle.*—From short to average length; average caliper; erect; usually smooth; with several to many small stipitate glands and several to many small prickles. Color—near Deep Chrysolite Green, Plate XXXI (R), overlaid with near Buffy Olive, Plate XXX (R) on side exposed to sun.

*Before calyx breaks.*—Size—from small to medium. Form—short; between ovoid and globular.

*As calyx breaks.*—Color—near Purple Madder, Plate 1028/1, page 181 (W), with areas not exposed to sun near Brick Red, Plate 016/2, page 106 (W).

*Sepals.*—Inner surface—with fine, wooly tomentum. Outer surface—usually smooth; with none to few small stipitate glands and none to few fine hairs. Alternate margins—lined with fine, wooly tomentum. Other margins—lined with several to many small stipitate glands and short slender foliaceous parts; sepals sometimes with slender foliaceous appendages extending from ¼ to ½ of sepal length.

*As first petal opens.*—Size—average. Form—medium length; from ovoid to urn-shaped. Color: Outside—near Indian Yellow, Plate 6/2, page 6 (W), with marking of near China Rose, Plate 024/1, page 111 (W) on areas exposed to sun longer, blending with near Buttercup Yellow, Plate 5/1, page 5 (W) toward base of petal; inside—near Signal Red, Plate 719/1, page 93 (W), blending with near Crimson, Plate 22/1, page 22 (W) toward apex of petal, with area at base of petal near Buttercup Yellow, Plate 5/1, page 5 (W) extending from ¼ to ½ of petal length toward apex.

*Opening.*—Opens up well; is not retarded or prevented from opening by cold, hot, wet or dry weather.

Bloom:

*Size (when fully open).*—Average; from 4 inches to 5 inches.

*Petalage.*—Double; from 25 to 30 petals, plus 8 to 12 petaloids; arranged irregularly.

*Form.*—Cupped and high-centered at first, but becoming from flat to cupped; petals being at first somewhat loosely cupped, with tips reflexed slightly outward, but later becoming loosely flat to cupped, with tips reflexed slightly outward at maturity.

Petals:

*Texture.*—Medium thickness; moderately leathery.

*Appearance.*—Inside—from satiny to velvety. Outside—satiny.

*Shape.*—Outside—between round and broadly obovate, with apex flat. Intermediate—broadly obovate, with apex from rounded to flat. Inside—broadly obovate, with apex rounded.

This description was made of a newly opened flower grown outdoors during the month of June at Ontario, California:

*Color.*—Outdoor petal: outside surface—near Saffron Yellow, Plate 7/2, page 7 (W), with markings of near Scarlet, Plate 19/1, page 19 (W) on upper ⅔ of petal, with lower ⅓ of petal blending with near Lemon Yellow, Plate 4, page 4 (W) toward base; inside surface—near Scarlet, Plate 19, page 19 (W), blending with near Rose Madder, Plate 23/1, page 23 (W) toward apex of petal, with lower ¼ to ⅓ of petal near Lemon Yellow, Plate 4, page 4 (W). Intermediate petal: Outside surface—near Indian Yellow, Plate 6/2, page 6 (W), with markings of near Vermilion, Plate 18/2, page 18 (W) on upper ⅔ of petal, with lower ⅓ of petal blending with near Lemon Yellow, Plate 4, page 4 (W); inside surface—near Scarlet, Plate 19, page 19 (W), blending with near Carmine, Plate 21, page 21 (W) toward apex of petal, with lower ¼ to ⅓ of petal near Lemon Yellow, Plate 4, page 4 (W). Inner petal: Outside surface—near Buttercup Yellow, Plate 5/2, page 5 (W), with markings of near Mandarin Red, Plate 17/2, page 17 (W) on upper ⅔ of petal, with lower ⅓ of petal near Aureolin, Plate 3, page 3 (W); inside surface—near Scarlet, Plate 19, page 19 (W), blending with near Geranium Lake, Plate 20/1, page 20 (W) toward apex of petal, with lower ¼ to ⅓ of petal near Aureolin, Plate 3, page 3 (W).

This description was made from a rose that was open for three days outdoors during the month of June at Ontario, California:

*Color.*—Outer petal: Outside surface—near Cadmium Orange, Plate 8/3, page 8 (W), with markings of near Tyrian Rose, Plate 24/3, page 24 (W) on upper ½ of petal, with lower ½ of petal near Lemon Yellow, Plate 4/2, page 4(W); inside surface—between Rose Madder, Plate 23/1, page 23 (W) and Rose Bengal, Plate 25/1, page 25 (W), with lower ¼ of petal near Lemon Yellow, Plate 4, page 4 (W). Inner petal: Outside surface—near Indian Yellow, Plate 6/3, page 6 (W), with markings of near Scarlet, Plate 19/2, page 19 (W) on upper ⅔ of petal, with lower ⅓ of petal near Lemon Yellow, Plate 4/1, page 4 (W); inside surface—near Geranium Lake, Plate 20/1, page 20 (W), with lower ¼ of petal near Lemon Yellow, Plate 4/1, page 4 (W).

*General color effect.*—Newly opened flower—between Scarlet, Plate 19/1, page 19 (W) and Carmine, Plate 21/1, page 21 (W). 3-days open—between Geranium Lake, Plate 20/1, page 20 (W) and Rose Bengal, Plate 25/2, page 25 (W). More than 3-days open—between Neyron Rose, Plate 623/1, page 76 (W) and Phlox Pink, Plate 625/1, page 77 (W).

*Behavior.*—Drop off cleanly; not particularly affected by cold, hot, wet or dry weather.

*Flower longevity.*—On bush in garden—2 or 3 days in July. Cut roses grown outdoors and kept at livingroom temperatures—2 or 3 days in July.

*Reproductive organs*

Stamens: From average number to many; arranged regularly about pistils; a few mixed with petaloids.

Filaments: Medium length (from 5 mm. to 12 mm.); most with anthers. Color—near Buttercup Yellow, Plate 5/1, page 5 (W).

Anthers: From small to medium size; all open approximately at once. Color: Upper side—margins near Tangerine Orange, Plate 9/2, page 9 (W), with remainder near Lemon Yellow, Plate 4/2, page 4 (W); underside—same as upper side.

Pollen: Abundant. Color—near Tangerine Orange, Plate 9, page 9 (W).

Pistils: From few to average number (approximately 35).

Styles: Uneven; from short to average length; thin; bunched. Color—near Primrose Yellow, Plate 601/2, page 65 (W).

Stigma: Color—near Barium Yellow, Plate 503/2, page 131 (W).

Ovaries: Usually all enclosed in calyx.

Hips: Short; globular; walls thick and fleshy. Color (half mature)—near Citrine Drab, Plate XL (R).

Sepals: Falling soon; medium length; straight. Color: Inside—near Light Buff, Plate XV (R); outside—near Coral Red, Plate XIII (R).

Seeds: Few (from 4 to 10); small.

*Plant*

Foliage:

*Leaves*—Compound of usually 3 to 7 leaflets; abundant; medium size; leathery; glossy.

*Leaflets.* — Shape — oval. Apex — acute. Base—round. Margin—simply serrate.

*Color.*—Mature: Upper surface—near Light Cress Green, Plate XXXI (R); under surface—near Light Grape Green, Plate XLI (R). Young: Upper surface—near Deep Dull Yellow Green (1), Plate XXXII (R); under surface—near Absinthe Green, Plate XXXI (R).

*Rachis (the supporting steam of the compound leaf).* — Average size. Upper side — smooth; grooved; with none to few stipitate glands on edges. Under side—smooth; with none to few prickles.

*Stipules.*—Medium length; from medium width to wide; with short points turning out at an angle of more than 45°.

*Disease resistance.*—Better than average resistance to mildew, as determined by comparison with other varieties grown under comparable cultural conditions at Ontario, California.

Growth:

*Habit.*—Bushy; upright-spreading; much branched.

*Growth.*—Vigorous.

*Canes.*—Medium caliper.

*Main stems.*—Color—near Mignonette Green, Plate XXXI (R). Large prickles—from several to many; medium length; almost straight; with narrow base of medium length; color—near Deep Olive Buff, Plate XL (R). Small prickles—few; color — near Deep Olive Buff, Plate XL (R). Hairs—none.

*Branches.*—Color—near Citrine, Plate IV (R), overlaid with near Prussian Red, Plate XXVII (R) on side exposed to sun. Large prickles—from several to many; from medium length to long; hooked slightly downward; with narrow base of medium length; color — near Hydrangea Red, Plate XXVII (R). Small prickles—from none to few; color—near Hydrangea Red, Plate XXVII (R). Hairs—none.

*New shoots.*—Color—near Absinthe Green, Plate XXXI (R), overlaid with near Cameo Brown, Plate XXVIII (R) on side exposed to sun. Large prickles—few; from short to medium length; hooked; slightly downward; with narrow base of medium length; color—near Mineral Red, Plate XXVII (R). Small prickles—from several to many; color—near Mineral Red, Plate XXVII (R). Hairs—none.

I claim:

A new and distinct variety of rose plant of the floribunda class, substantially as herein shown and described, characterized particularly as to novelty by the unique combination of a very attractive, vigorous, bushy and rounded plant habit, attractive, dense, glossy, dark green foliage which clothes the plant well, nearly urn-shaped flower buds, double flowers of attractive form, said flowers being of exceptionally large size for a floribunda variety, and being borne in small to medium sized clusters which cover the plant very well, and a distinctive and attractive multi-colored floral effect of the flowers, with red and yellow colors in the bud, red in the newly open flower, but changing to attractive pinks as the flowers age.

No references cited.

ABRAHAM G. STONE, *Primary Examiner.*

R. E. BAGWILL, *Assistant Examiner.*